United States Patent [19]
Jones

[11] Patent Number: 5,882,667
[45] Date of Patent: Mar. 16, 1999

[54] PLASTIC SLEEVE CONTAINING AN ANTIMICROBIAL AGENT

[76] Inventor: Thomas Lucius Jones, 3 Indian Pl., Asheville, N.C. 28805

[21] Appl. No.: 101,495

[22] Filed: Aug. 2, 1993

[51] Int. Cl.[6] .................................................. A01N 25/34
[52] U.S. Cl. ........................ 424/405; 424/411; 424/78.24; 424/78.35; 424/78.36
[58] Field of Search ................................ 424/405, 78.24, 424/78.31, 78.35, 78.36, 499, 501, 411

[56] References Cited

U.S. PATENT DOCUMENTS

| | | | |
|---|---|---|---|
| 2,979,030 | 4/1961 | Harrington | 120/42.03 |
| 3,030,925 | 4/1962 | Dyson | 120/42 |
| 3,482,258 | 12/1969 | Steen | 346/140 |
| 3,888,416 | 6/1975 | Lin | 239/34 |
| 4,768,531 | 9/1988 | Broussard | 132/84 |
| 4,832,942 | 5/1989 | Crace | 428/40 |
| 5,017,369 | 5/1991 | Marhenka | 424/78 |
| 5,161,971 | 11/1992 | Neimer et al. | 433/141 |
| 5,173,291 | 12/1992 | Brink et al. | 424/78.06 |
| 5,236,703 | 8/1993 | Usala | 424/78.36 |
| 5,242,052 | 9/1993 | Weder | 206/423 |
| 5,294,445 | 3/1994 | Sievens et al. | 424/411 |

*Primary Examiner*—Neil S. Levy
*Attorney, Agent, or Firm*—Carter & Schnedler, PA.

[57] ABSTRACT

A plastic sleeve covering containing an antimicrobial agent to resist or prevent the growth of microbes on the surface thereof, thereby preventing cross-contamination of subsequent users following the use of the item by an infected individual and especially items commonly used, such as writing pens, door handles, push-plate appliances for doors, and flush handles accompanying toilets in public facilities.

7 Claims, 3 Drawing Sheets

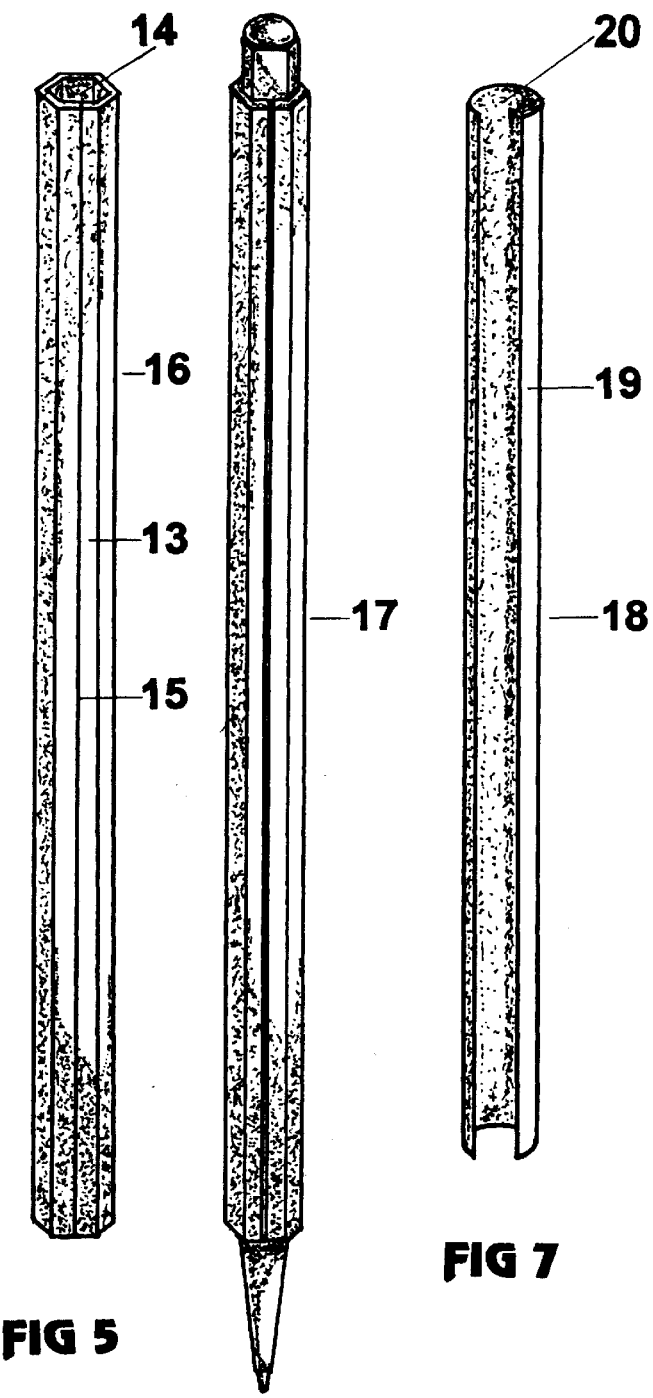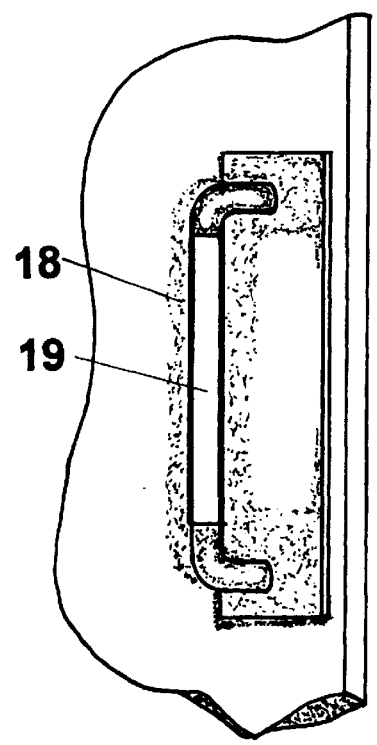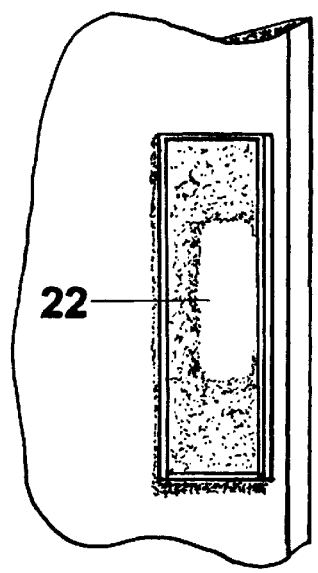
FIG 5
FIG 6
FIG 7
FIG 8
FIG 9

5,882,667

PLASTIC SLEEVE CONTAINING AN ANTIMICROBIAL AGENT

FIELD OF THE INVENTION

The present invention relates to methods and apparatus to prevent cross contamination between users of writing instruments and the gripping portion of other commonly used public items.

BACKGROUND OF THE INVENTION

Writing instruments were in evidence in prehistoric cave drawings. While they, no doubt, facilitated the spread of communicable diseases, they have not been commonly recognized as instruments of transmission. A more commonly recognized instrument of disease transmission is the flush handle associated with a toilet and, to a lesser extent, door knobs or push-plates. Our daily lives are replete with opportunities for infection simply through the communal use of familiar objects which we do not find ominous because of their familiarity. A study demonstrating the potential for communicating an infection via handled objects has been conducted using card-playing college students as subjects. The study demonstrated that the communication of a viral infection, the common cold, was greater when the subjects handled common playing cards, than through the much more intimate contact of kissing. The results were attributed to the card players with colds effectively transmitting the virus to the non-infected players by contaminating the cards with the virus where it transfers to the hands of the non-infected players, whereupon the non-infected players infected themselves when they rubbed the mucus membranes of the nose and eyes.

Current events are often centered around communicable diseases and the suffering they are causing, and sometimes death. Many infections associated with the restaurant industry are apparently communicated to the public through the common use, by the subjects, of an object used initially by the diseased subject with unclean hands. Writing pens are among the most commonly used public items and are not thought of as instruments of communicable diseases. The common habit people have of unconsciously putting pens into their mouth and the open space between the end of the shaft and the small cap on the upper end of the pen, which would maintain a furtile environment for a host of pathogens, makes them one of the most potent sources of communicable disease. Other common habits such as putting fingers in the mouth, rubbing the nose, rubbing the eyes, and scratching or touching open wounds, all make the hands a potent source of infection. Also, other commonly used items, such as door knobs, flush-handles on toilets, by contaminated hands, are a source of communication of disease pathogens.

The potential for the transmission of disease via common items becomes greatly enhanced when visiting or working in an environment where the focus of that environment is treating diseased individuals. In fact, the common writing pen is probably the weakest link in a sterile environment in the health-care field.

Inks typically have a low vapor pressure to allow them to dry quickly and prevent smudging. This attribute also makes autoclaving the ink, as set forth in U.S. Pat. No. 5,161,971 to Neimer et al, at necessarily high temperatures without damaging the ink, impossible. Further, it is not common for the public offices of any description, other than health-care, to have an autoclave available for sterilizing a writing pen.

U.S. Pat. No. 3,482,258 to Steen addresses a method for maintaining a sterile ink supply. While that is important in maintaining a free-flowing ink supply, it was not intended to address the problem of communication of disease pathogens between users of the writing device.

Ink repellent coatings have been developed for writing pens, as shown in U.S. Pat. Nos. 2,979,030 to Harrington and 3,030,925 to Dyson, to prevent ink from adhering to the pen which could soil documents being created or edited with the writing pen, or soil the user's fingers and clothing.

Others have used pens as part of a novel, multi-use item for grooming, as shown in U.S. Pat. No. 4,768,531 to Broussard. The Broussard pen was apparently meant as a handy travel utility.

A pen which emitted a fragrance intended to adjust the sensitivities of the user to a more pleasant memory is the subject of U.S. Pat. No. 3,888,416 to Lin. The inventor suggests that the fragrance emitted by the pen would help the user forget unsettling surroundings which have characteristic odors, such as a hospital or a sick ward.

A perforated tape that delivered a sterilizing liquid or foam from an underlying sponge area is the subject of U.S. Pat. No. 4,832,042 to Crace. Such a tape would be common knowledge to anyone who has ever used an adhesive bandage and had the previously applied antiseptic seep through the holes in the top to soil their fingers. It would prove impractical for use under any, but very specialized, conditions where the liquid or foam deposited on the individual contacting the tape would not cause a problem being transferred to other objects being handled by the individual. Additionally, the drying of the solution in the sponge layer and/or repeated use, would rapidly render the tape ineffective.

In spite of attempts to modify writing instruments for a variety of purposes, it is believed that no writing pen has ever been proposed which would conveniently and consistently prevent the writing pen from becoming a vehicle for the transportation of a broad spectrum of communicable pathogens throughout the useful life of the writing pen without notably soiling the user. In addition, it is not believed that commonly used public items, such as door knobs or flush-handles on toilets, have been modified to resist the growth of pathogens placed on those objects by touching and thereby reduce the potential of them becoming vehicles of infection.

It has been customary to add preservatives to plastics to protect the plastic itself against attack by microorganisms. Plastic additives such as plasticizers can affect the susceptibility of a plastic to microbes. The test typically associated with a desire to protect the plastic, test the ability of fungi to use the polymeric material as a food source and the ability of stain-producing microorganisms to stain the polymeric material, is termed "the pink stain test". Other tests, such as a soil burial or humidity cabinet test, may be done. None of these tests or preservatives are directed at viruses which can live only in vital tissue, but may use a plastic device as a vehicle to infect. It is not believed that any attempt has been made to address the viability of human pathogens on commonly used objects such as writing pens, door knobs, or flush-tank handles.

Currently evolving communicable diseases such as AIDS define a need to develop some protection from disease pathogens omnipresent on commonly used public items. While AIDS is currently not as easily transmitted as many other viral infections, the incidence of recorded infections has risen from 1 million recorded cases world-wide, to a current figure of 14 million, in a relatively short period. The ability of the AIDS virus to undergo rapid mutation could produce a strain which readily infects, as cold or measle viruses do.

OBJECTS OF THE INVENTION

It is therefore one object of this invention to provide a substrate for commonly used items for the prevention of cross contamination among users.

It is another object to provide a sleeve to cover portions of objects to prevent cross contamination.

SUMMARY OF THE INVENTION

In one form of the present invention, a sterile substrate which is preferably in the form of a sleeve covering for a writing pen and other public use items such as door knobs or flush-tank handles, is provided to prevent the touched portion from becoming a vehicle for communicable diseases. The substrate or sleeve contains an antimicrobial agent effective against microbes likely encountered. The sterile substrate or sleeve may be used as a covering for writing pens, door knobs, flush-tank handles and other such publicly handled items, and addresses a void existing in the prior art by providing such a covering which will not transport microbes.

The sterile sleeve covering for writing pens may also contain an unpleasant tasting substance such as mustard oil or pepper extract to discourage a user from placing the pens in the mouth. The sterile sleeve covering may be brightly colored to alert persons using the item that the surface of the item contains an antimicrobial agent and that anyone allergic to the antimicrobial agent should protect their bare hand and not put the sleeve into their mouth.

Although preferred aspects of the present invention include all modifications to the sterile sleeve covering discussed below, the invention contemplates using one, all, or any combination of the modifications.

The above and other aspects of sterile sleeve covering invention are achieved by the structure as described below in combination with the accompanying drawings showing preferred embodiments of the present invention.

BRIEF DESCRIPTION OF THE DRAWINGS

FIG. 5 is a pictorial view of a sleeve incorporating another embodiment of the subject invention, which may be placed over a non-round pen.

FIG. 6 is a pictorial view showing the sleeve of FIG. 5 in place over a non-round pen.

FIG. 7 is a pictorial view of yet another embodiment of the subject invention, showing a sterile sleeve covering which may be rolled into a close circumference to fit the geometric shape of an object, or may be flattened to cover a flat surface or curved to fit curved surfaces.

FIG. 8 is a partial pictorial view showing the sleeve of FIG. 7 in place about a door handle.

FIG. 9 is a partial pictorial view showing the sleeve of FIG. 7 flattened out on a push plate door appliance.

DETAILED DESCRIPTION OF THE PREFERRED EMBODIMENTS

Figures 1, 2, 3, 4:
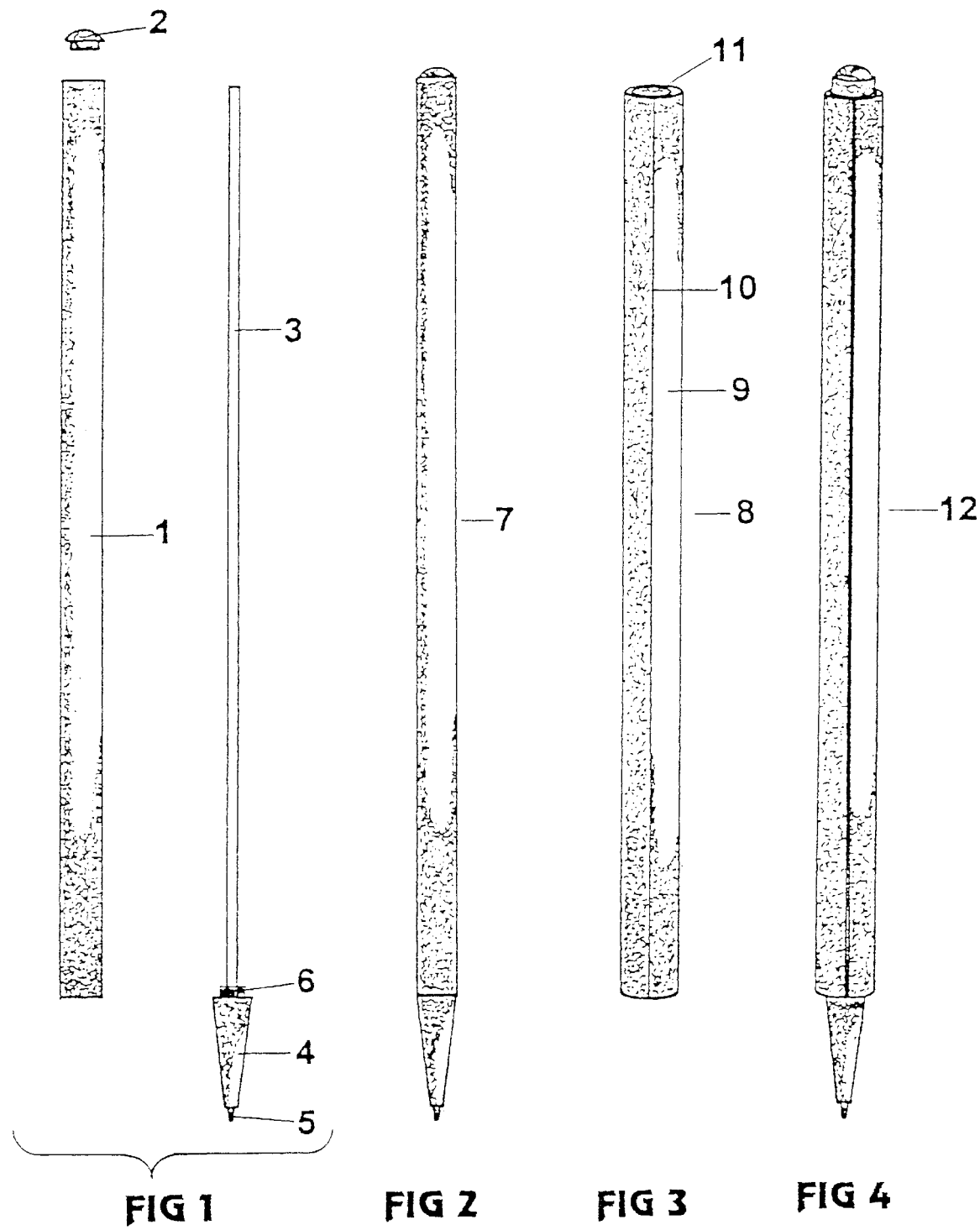
FIG. 1 is an exploded view of a sterile writing pen incorporating one embodiment of the subject invention.
FIG. 2 is a plan view of the pen of FIG. 1.
FIG. 3 is a pictorial view of a sleeve incorporating another embodiment of the subject invention, which may be placed over a round pen.
FIG. 4 is a pictorial view of the sleeve of FIG. 3 in place about a round pen.

Referring to FIGS. 1 and 2, a substrate hollow sterile writing pen shaft 1 is preferably injection molded, as is the writing pen shaft cap 2, using a mixture produced from a combination of an antimicrobial agent and a plastic. The preferred antimicrobial agents include iodines, povidone-iodines, thimerosals, merbromins, silver proteins, hexachlorophenes, chlorhexidine gluconates, benzalkonium chlorides, glutaraldehydes, sodium hypochlorites, iodophors, phenolic compounds, formaldehydes, chlorine dioxides, sodium nitrites, and oxychlorosene sodiums, and any combinations of these antimicrobial agents. The preferred plastics include acetals, acrylics, cellulosics, floroplastics, ketone based resins, nitrile resins, nylons, polyamide-imides, polyarylates, polybutylenes, polycarbonates, polyesters, polyetherimides, polyethylenes, polyimides, polymethylpentenes, polyphenylene oxides, polyphenylene sulfides, polypropylenes, styrenic resins, sulfone-based resins, thermoplastic elastomers, allyls, bis-maleimides, vinyl based resins, epoxys, phenolics, polyesters, polyurethanes, formaldehydes, silicones, ureas, melamines, and any combinations of the these plastics.

In the construction of the writing pen shaft 1, the plastic and the antimicrobial agent are first mixed and the shaft 1 is extruded from the mix using a commercially available plastic extrusion machine, into a cylinder and cut into lengths suitable for a writing pen shaft as depicted. The shaft-cap 2 and cone 4 are produced by injection molding the same mix of material in a die mold.

Preferably, the mixture is from 1% to 10% by weight of antimicrobial agent; however, more preferably, the mixture is from 3% to 10% by weight of antimicrobial agent. In addition, preferably the plastic is from 90% to 99% by weight.

Additionally, an antistatic agent may be added to the mixture to prevent microbes from being attracted to the plastic surface. The preferred antistatic agents include long-chain alkyl quaternary ammonium salts, phosphonium salts, sulfonium salts, alkali salts of alkyl sulphonics, phosphonics, dithiocarbamics, carboxylic acids, ethoxylated fatty amines, fatty acid esters, ethanolamides, polyethylene glyo-esters, monoglycerides, or di-glycerides, or any combinations of these antistatic agents. Preferably the mixture includes from 0.1% to 1% by weight of antistatic agent.

A bright colorant, or colorants, may be added to the mixture to warn potentially allergic users that the product contains an antimicrobial agent, or agents, and to caution all users to keep it out of their mouth. The preferred colorants are titanium dioxides, zincs, sulfides, iron oxides, chromates, cadmiums, chromium oxides, ultramarines, mixed metal oxides, or carbon blacks, or any combinations of these colorants. The preferred range of colorants in the mixture is from 0.001% to 0.005%.

To discourage persons and animals further from putting the product in their mouth, foul tasting mustard oils or pepper extracts may be added to the mixture. Preferably, the foul-tasting materials are from 0.01% to 0.05% by weight of the mixture.

Further, a clay which is preferably KAOLIN, which is often used as medicinal filler, may be added to the mixture to cause the sterile sleeve to wear more readily, thereby exposing a fresh supply of antimicrobial agent to the surface more frequently than a wear pattern without the clay would permit. Preferably, the clay is from 5% to 50% by weight of the mixture. If the clay filler is more than 10% by weight, then the plastic weight percent should be reduced accordingly.

Also additional additives such as antioxidants, chlorinated paraffins, coupling agents, flame retardants, foaming agents, lubricants, modifiers, mold polish, mold release agents, organic peroxidants, plasticizers, or stabilizers may be added to the mixture to preserve the plastic or the equipment used to work the plastic, or to address other health considerations such as smoke and flame retardation. Preferably, these additional additives should be from 1/10% to 1% by weight.

The ink cylinder 3 is attached to the point 5 and is wedged or glued into a centrally located passage in the cone 4. This assembly is placed into a centrally located passage in the hollow writing pen shaft 1 as is the collar 6 on the cone 4 until the cone 4 contacts the lower end of the writing pen shaft 1. The collar 6 is either wedged into, or glued into, the centrally located passage in the writing pen shaft. The cap 2 is placed on the remaining open end of the shaft 1 by wedging or gluing the cap into the centrally located passage in the shaft cylinder 1 to produce the sterile writing pen 7.

In an alternative embodiment shown in FIGS. 3 and 4, a plastic extruding machine is used to produce an essentially round, rigid, sterile plastic sleeve cylinder 8, using the plastic antimicrobial mixture set forth above and preferably the other additives also set forth above. Cylinder 8 includes a round centrally located passage 11 and a groove 10 which runs the length of the cylinder and extends from the outside surface 9 to the inner passage 11, using the aforementioned plasticantimicrobial mixture. The groove 10 allows the diameter of the passage 11, centrally located in the rigid, sterile plastic sleeve 8, to enlarge to accept an essentially round non-sterile writing pen 12 thereby presenting the user with a sterile gripping surface 9. This embodiment is intended as a retrofit for existing essentially round writing pens.

Referring to FIGS. 5 and 6, in a second alternative embodiment, a similar rigid, sterile plastic sleeve covering 16, using the aforementioned mixture, may be formed using a plastic extrusion machine, with sterile plastic sleeve covering to have a six-sided centrally located passage 14 and a groove 15 running the length of the sleeve and extending from the outer surface 13 to the inner surface of the centrally located passage 14. The groove 15 would allow the centrally located passage 14 in the sleeve 16 to enlarge to accept an existing writing pen with a non-round six-sided surface 17, thereby presenting the user with a sterile gripping surface 13.

In a third alternative embodiment as shown in FIG. 7, a sterile sleeve covering may be made, from the aforementioned mixture, into a plastic sheet 18 which may be rolled into a closed circumference to fit the geometric shape of objects with a regular or irregular surface design, or it may be flattened to cover flat surfaces or curved to fit a curved surface. The sterile plastic sheet covering may have one surface covered with an adhesive 20 in order to better attach it to the object to be covered and present the user with a sterile surface 19. The intended use of the flexible, sterile sleeve covering is to retrofit existing objects with non-sterile surfaces.

FIG. 8 illustrates a door handle of the type commonly found in public bathrooms, wrapped in a flexible, sterile plastic sleeve covering 18 so as to present the user with a sterile gripping surface 19.

FIG. 9 illustrates a push-plate door appliance 22 of the type commonly found in public bathrooms, where the flexible, sterile sleeve covering 18 has been flattened to cover the push-plate to present the user with a sterile touching surface.

Figure 10:
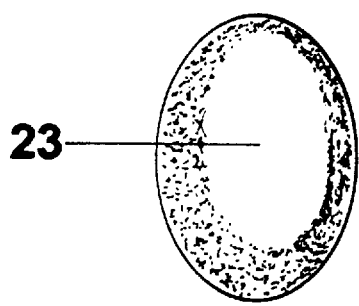
FIG. 10 shows another alternative embodiment of the subject invention in the form of a rigid sterile plastic shell sleeve.
Figure 11:
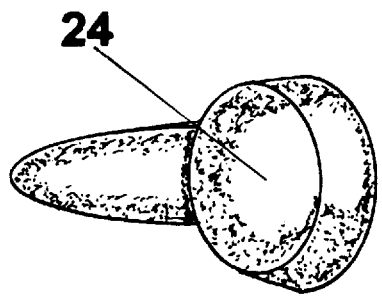
FIG. 11 is a pictorial view showing another embodiment of the apparatus shown in FIG. 10.

In a fourth alternative embodiment as shown in FIGS. 10 and 11, a rigid sterile plastic sleeve 23 is shown which may be injection molded from the aforementioned mixture to custom fit the geometric design of the exterior of an existing handle 25 of the type found on doors. Also in this embodiment, and illustrated, is a rigid, sterile plastic shell sleeve 24 which may be injection molded from the aforementioned mixture to custom fit the geometric design of the exterior of an existing handle 26 of the type found in public facilities, such as bathrooms.

Figure 12:
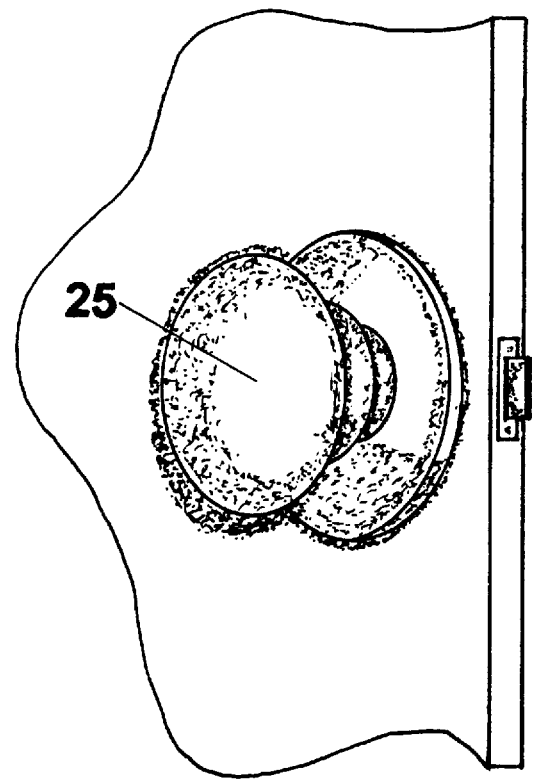
FIG. 12 is a partial pictorial view showing another embodiment of the invention whereby a door handle has been molded utilizing the subject invention.
Figure 13:
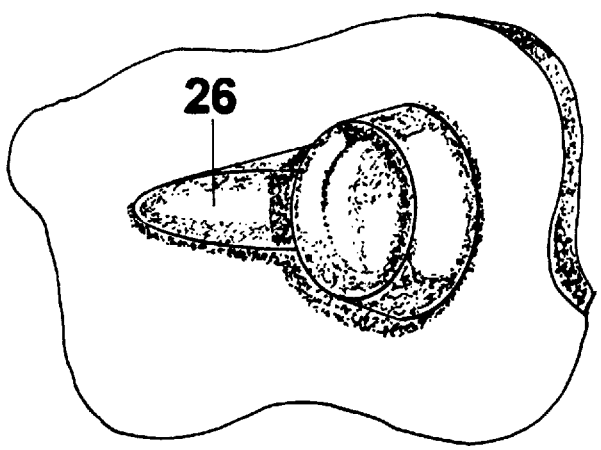
FIG. 13 is a partial pictorial view showing yet another embodiment of the apparatus shown in FIG. 12.

In a fifth alternative embodiment as shown in FIGS. 12 and 13, the aforementioned mixture may be used to mold the handles 25 and 26, making it unnecessary to cover them with an appliance to present a sterile gripping surface.

The invention described above is merely illustrative of applicant's invention. The invention itself, together with other embodiments and equivalencies thereof, is set forth in the claims below.

What is claimed is:

1. A sterile rigid sleeve produced from a mixture of a plastic and an antimicrobial agent for avoiding cross-contamination between persons who come in contact with said sleeve; said plastic being formed from styrenic resins; said antimicrobial agent is taken from the group consisting of iodines and povidone-iodines and any combinations of said antimicrobial agents; said sterile rigid sleeve being in the form of an elongated rigid cylinder which is the shaft of a writing pen; said mixture being from 1% to 10% by weight of antimicrobial agent.

2. A sterile rigid sleeve produced from a mixture of a plastic and an antimicrobial agent for avoiding cross-contamination between persons who come in contact with said sleeve; said plastic being formed from styrenic resins; said antimicrobial agent is taken from the group consisting of iodines and povidone-iodines and any combinations of said antimicrobial agents; said sterile rigid sleeve being elongated for covering non-sterile surfaces; said mixture being from 1% to 10% by weight of antimicrobial agent.

3. A sterile rigid sleeve as set forth in claim 2, wherein said sleeve has a centrally located passage which is essentially round for receiving essentially round writing pens.

4. A sterile rigid sleeve as set forth in claim 3, including a groove the length of the sleeve and extending from the outer surface of the sleeve to said centrally located passage to allow the centrally located passage to be enlarged.

5. A sterile rigid sleeve as set forth in claim 2, wherein said sleeve is rigid and wherein said sleeve has a centrally located passage which is non-round for receiving non-round writing pens.

6. A sterile rigid sleeve sleeve as set forth in claim 5, wherein said sleeve includes a groove the length of the sleeve and extending from the outer surface to said centrally located passage to allow the centrally located passage to be enlarged.

7. A sterile rigid sleeve as set forth in claim 2, including an adhesive on the side of the sleeve in juxtaposition to the object to which the sleeve is applied.

* * * * *